United States Patent
Santiago et al.

(10) Patent No.: US 6,610,329 B2
(45) Date of Patent: *Aug. 26, 2003

(54) COMPOSITIONS FOR THE DELIVERY OF ANTIGENS

(75) Inventors: Noemi B. Santiago, Boqueron, PR (US); Susan Haas, Monsey, NY (US); Andrea Leone-Bay, Ridgefield, CT (US); Sam J. Milstein, Larchmont, NY (US); Evgueni Barantsevitch, Scarsdale, NY (US)

(73) Assignee: Emisphere Technologies Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/862,013

(22) Filed: May 21, 2001

(65) Prior Publication Data

US 2002/0001591 A1 Jan. 3, 2002

Related U.S. Application Data

(63) Continuation of application No. 09/346,971, filed on Jul. 2, 1999, now abandoned, which is a continuation of application No. 08/438,644, filed on May 10, 1995, now Pat. No. 5,958,457, which is a continuation-in-part of application No. 08/335,147, filed on Oct. 25, 1994, now abandoned, and a continuation-in-part of application No. PCT/US94/04560, filed on Apr. 22, 1994, which is a continuation-in-part of application No. 08/051,019, filed on Apr. 22, 1993, now Pat. No. 5,451,410, and a continuation-in-part of application No. 08/205,511, filed on Mar. 2, 1994, now Pat. No. 5,792,451, said application No. 08/438,644, and a continuation-in-part of application No. 08/231,622, filed on Apr. 22, 1994, now Pat. No. 5,629,020.

(51) Int. Cl.[7] .................................................. A61K 9/14
(52) U.S. Cl. ........................ 424/490; 424/463; 424/489; 424/490; 424/499; 424/477; 424/485

(58) Field of Search ................................. 424/463, 489, 424/490, 499, 477, 485

(56) References Cited

U.S. PATENT DOCUMENTS

| | | | |
|---|---|---|---|
| 4,183,849 A | 1/1980 | Hansen et al. | 530/305 |
| 4,238,506 A | 12/1980 | Stach et al. | 424/319 |

(List continued on next page.)

FOREIGN PATENT DOCUMENTS

| | | |
|---|---|---|
| EP | 0036145 | 9/1981 |
| EP | 226223 | 6/1987 |

(List continued on next page.)

OTHER PUBLICATIONS

Palagiano, F. et al.: "Synthesis, stability and anticonvulsant activity of two new GABA prodrugs," Pharamazic, 52 (4): 272–276 (1997), XP–001084051.

Yalcin, I. et al.: "Synthesis and Microbiological Activity of Some Novel N–(2–Hydroxyl–5–Substitutedphenyl)Benzacetamides, Phenoxyacetamides and Thiophenoxycetamides as the Possible Metabolites of Antimicrobial Active Benzoxazoles," Il farmaco, 52 (11), 685–689 (1997).

(List continued on next page.)

Primary Examiner—Thurman K. Page
Assistant Examiner—Lakshmi S. Channavajjala
(74) Attorney, Agent, or Firm—Darby & Darby

(57) ABSTRACT

The present invention relates to compositions and methods for orally delivering antigens. The antigen and an adjuvant are combined with an acylated amino acid or polyamino acid and, a sulfonated amino acids or polyamino acid, or a salt of the foregoing.

14 Claims, 3 Drawing Sheets

U.S. PATENT DOCUMENTS

| | | | |
|---|---|---|---|
| 4,757,066 A | 7/1988 | Shiokari et al. | 514/210 |
| 4,835,312 A | 5/1989 | Itoh et al. | 564/205 |
| 4,878,942 A | 11/1989 | Motegi et al. | 71/109 |
| 4,900,730 A | 2/1990 | Miyauchi | 514/12 |
| 4,927,928 A | 5/1990 | Shroot et al. | 544/154 |
| 5,066,487 A | 11/1991 | Morelle et al. | 424/68 |
| 5,352,461 A | 10/1994 | Feldstein et al. | 424/493 |
| 5,447,728 A | 9/1995 | Milstein et al. | 424/490 |
| 5,451,410 A | 9/1995 | Milstein et al. | 424/490 |
| 5,541,155 A | 7/1996 | Leone-Bay et al. | 514/2 |
| 5,629,020 A | 5/1997 | Leone-Bay et al. | 424/489 |
| 5,643,957 A | 7/1997 | Leone-Bay et al. | 514/563 |
| 5,650,386 A | 7/1997 | Leone-Bay et al. | 514/2 |
| 5,665,700 A | 9/1997 | Cho et al. | 514/2 |
| 5,693,338 A | 12/1997 | Milstein | |
| 5,705,529 A | 1/1998 | Matyus et al. | 514/541 |
| 5,709,861 A | 1/1998 | Santiago et al. | 424/184.1 |
| 5,714,167 A | 2/1998 | Milstein et al. | 424/490 |
| 5,750,147 A | 5/1998 | Kantor | 424/491 |
| 5,766,633 A | 6/1998 | Milstein et al. | 424/489 |
| 5,773,647 A | 6/1998 | Leone-Bay et al. | 562/444 |
| 5,792,451 A | 8/1998 | Sarubbi et al. | 424/85.4 |
| 5,811,127 A | 9/1998 | Milstein et al. | 424/490 |
| 5,863,944 A | 1/1999 | Leone-Bay et al. | 514/559 |
| 5,866,536 A | 2/1999 | Leone-Bay et al. | 514/2 |
| 5,958,457 A * | 9/1999 | Santiago et al. | 424/490 |
| 5,990,166 A | 11/1999 | Leone-Bay et al. | 514/563 |
| 6,001,347 A | 12/1999 | Leone-Bay et al. | 424/85.1 |
| 6,051,258 A | 4/2000 | Kantor | 424/491 |
| 6,051,561 A | 4/2000 | Leone-Bay et al. | 514/56 |
| 6,060,513 A | 5/2000 | Leone-Bay et al. | 514/559 |
| 6,071,510 A | 6/2000 | Leone-Bay et al. | 424/85.2 |
| 6,071,538 A | 6/2000 | Milstein et al. | 424/464 |
| 6,090,958 A | 7/2000 | Leone-Bay et al. | 554/112 |
| 6,099,856 A | 8/2000 | Milstein et al. | 424/450 |
| 6,100,285 A | 8/2000 | Kantor | 514/400 |
| 6,100,298 A | 8/2000 | Leone-Bay et al. | 514/563 |
| 6,180,140 B1 | 1/2001 | Leone-Bay et al. | 424/489 |
| 6,221,367 B1 | 4/2001 | Milstein et al. | 424/489 |
| 6,242,495 B1 | 6/2001 | Leone-Bay et al. | 514/617 |
| 6,245,359 B1 | 6/2001 | Milstein et al. | 424/490 |

FOREIGN PATENT DOCUMENTS

| | | | |
|---|---|---|---|
| EP | 0365183 | 10/1989 | |
| EP | 0517211 | 9/1992 | |
| EP | 0576941 | 6/1993 | |
| ES | 369853 | 7/1969 | |
| FR | 4446 | 11/1966 | |
| GB | 2095994 | 10/1982 | |
| JP | 48-37819 | 11/1973 | |
| JP | 2239980 | 9/1990 | |
| WO | 9219263 | 12/1992 | |
| WO | 9747270 | 12/1997 | |
| WO | 8807378 | 10/1998 | |
| WO | WO 99/29705 | 6/1999 | C07H/15/00 |
| WO | 0006184 | 2/2000 | |
| WO | 0006534 | 2/2000 | |
| WO | 0007979 | 5/2000 | |
| WO | 0040203 | 7/2000 | |
| WO | 0046182 | 8/2000 | |
| WO | 0047188 | 8/2000 | |
| WO | 0048589 | 8/2000 | |
| WO | 0050386 | 8/2000 | |
| WO | 0059480 | 10/2000 | |
| WO | 0059863 | 10/2000 | |
| WO | 0132130 | 5/2001 | |
| WO | 0132596 | 5/2001 | |
| WO | 0134114 | 5/2001 | |
| WO | 0144199 | 6/2001 | |
| WO | 0151454 | 7/2001 | |

OTHER PUBLICATIONS

Gurrieri and Siracusa: "Thermal Condensation of Some alpha–aminoacids with Phatalic Acid" Thermochimica Acta, 7 (1973) 231–239.

Brown, G. and Foubister, A.J. "Receptor Binding Sites of Hypoglycemic Sulfonylureas and Related[(Acylamino)alkyl []benzoic Acids J Med Chem 27, 79–81, 1984.

Amino Yusuke et al. Chem Pharm Bull 36 pp. 4426–4434 (1988).

Chem Abs 73548–12–6 (Apr. 1991).

Chem Abs 70204–54–5 (Apr. 1991).

Chem Abs 184360–83–342 (1975) Solubility and disassociation constants of some alicyclic acids.

Chemical Abstract, vol. 99(23) Abst. No. 191473h (1983).

Johansen, Marianne, et al. "The Kinetics of decompn. Of various N–Mannich bases of salicylamide" Int. J. Pharm. (1980), 7(2): 119–27 (1980).

Leone–Bay, Andrea; Santiago, Noemi; Achan, Douglas; Chaudhary, Kiran; DeMorin,Frenel; Falzarano, Lise; Haas, Susan; Kalbag, Suraj; Kaplan, David; Leipold, Harry; Lercara, Christine; O'Toole, Doris; Rivera, Theresa; Rosado, Connie; Sarubbi, Donald; Vuocolo, Edmund; Wang, NaiFang; Milstein, Sam and Baughman, Robert A; N–acylated alpha–amino acids as Novel Oral Delivery Agents for Proteins; Journal of Medicinal Chemistry (1995) 38: 4263–4269.

Leone–Bay, A. "N–Acylates alpah–amino acids as novel oral delivery agents for proteins" Journal of Medicinal Chemistry vol. 38, 4263–4269 (1995).

Santiago, N; Haas, S; Baughman, R.; "Vehicles for Oral Immunization" Vaccine Design: The Subunit and Adjuvant Approach (1995) 17: 413–438.

Haas, S.; Miura–Fraboni, J.; Zavala, F. K.; Murata, Leone–Bay,, A.and Santiago, N.; "Oral Immunization with a Model Protein Entrapped in Microspheres Prepared from Derivatized alpha–Amino Acids"; Vaccine, (1996) 14(2): 785–791.

Haas, S; Meleski, D; Kutzy, T; Lercara,C; O'Toole, D; Leipold H; "Novel Delivery Agents for Mucosal Immunization"; STP Pharma Sciences (1998) 8(1): 59–65.

* cited by examiner

COMPOSITIONS FOR THE DELIVERY OF ANTIGENS

This is a continuation of U.S. application Ser. No. 09/346,971, filed Jul. 2, 1999 now abandonded; which is a continuation of U.S. application Ser. No. 08/438,644, filed May 10, 1995, now U.S. Pat. No. 5,958,457; which is a continuation-in-part of (a) U.S. application Ser. No. 08/335,147, filed Oct. 25, 1994, now abandoned; (b) PCT application Ser. No. PCT/US94/04560 filed Apr. 22, 1994; which is a continuation-in-part of U.S. application Ser. No. 08/051,019, filed Apr. 22, 1993, now U.S. Pat. No. 5,451,410; and of U.S. application Ser. No. 08/205,511, filed Mar. 2, 1994, now U.S. Pat. No. 5,792,451; and (c) U.S. application Ser. No. 08/231,622, filed Apr. 22, 1994, now U.S. Pat. No. 5,629,020. These prior applications are hereby incorporated herein by reference, in their entirety.

FIELD OF THE INVENTION

The present invention relates to compositions useful for the delivery, and preferably the oral delivery, of antigens and adjuvants to animals. Methods for the preparation and for the administration of these compositions are also disclosed.

BACKGROUND OF THE INVENTION

Conventional means for delivering antigens to their intended targets are often severely limited by the presence of biological, chemical, and physical barriers. Typically, these barriers are imposed by the environment through which delivery must take place, the environment of the target for delivery, or the target itself.

Oral delivery of antigens would be the route of choice for administration to animals if not for physical barriers such as the mucous layer and the epithelial cells of the gastrointestinal (GI) tract. Oral delivery is also impeded by chemical barriers such as the pH in the GI tract and the presence in the oral cavity and the GI tract of powerful digestive enzymes. Furthermore, orally administered soluble and insoluble antigens can induce a non-responsive state or tolerance.

Methods for orally administering antigens have been developed which rely on the use of either attenuated microorganisms or polylactide/polyglycocide (PLA/PGA) microspheres to increase antigen presentation to and uptake by the appropriate antigen presenting cells. Attenuated organisms, unless properly delivered, can regain virulence, however. Additionally, broad spectrum use of PLA/PGA microspheres is not possible because these carriers require organic solvents that may alter or denature antigens. Furthermore, PLA/PGA systems are difficult to manufacture.

More recently, microspheres comprising artificial polymers of mixed amino acids (proteinoids) have been described for delivering biologically active agents including antigens. Santiago, et al. *Pharmaceutical Res*. Vol. 10, No. 8, (1993).

Adjuvants have been coadministered with antigens to increase the effectiveness of antigens, but adjuvants and antigen/adjuvant compositions are susceptible to the common problems of oral delivery described above.

Consequently, there is still a need in the art for simple, inexpensive, and easily prepared systems which can effectively deliver a broad range of antigens, particularly via the oral route.

SUMMARY OF THE INVENTION

The present invention provides compositions for delivering antigens. These compositions are suitable for delivery via the oral route and comprise:

(a) an antigen;
(b) an adjuvant; and
(c) at least one carrier comprising a member selected from the group consisting of;
   (i) an acylated amino acid or a salt thereof;
   (ii) a polyamino acid comprising at least one acylated amino acid or a salt thereof;
   (iii) a sulfonated amino acid or a salt thereof;
   (iv) a polyamino acid comprising at least one sulfonated amino acid or a salt thereof; or
   (v) any combination thereof.

These compositions can be orally administered to animals to produce or prime and/or to boost an immunogenic response and to achieve immunization. When these compositions are used to boost immunogenic responses the prime can be delivered by the compositions of the present invention or other compositions.

Also contemplated are methods for preparing mixtures of microspheres of an antigen, an adjuvant, and a carrier as described above, and optionally, a dosing vehicle.

DETAILED DESCRIPTION OF THE INVENTION

Figure 1:
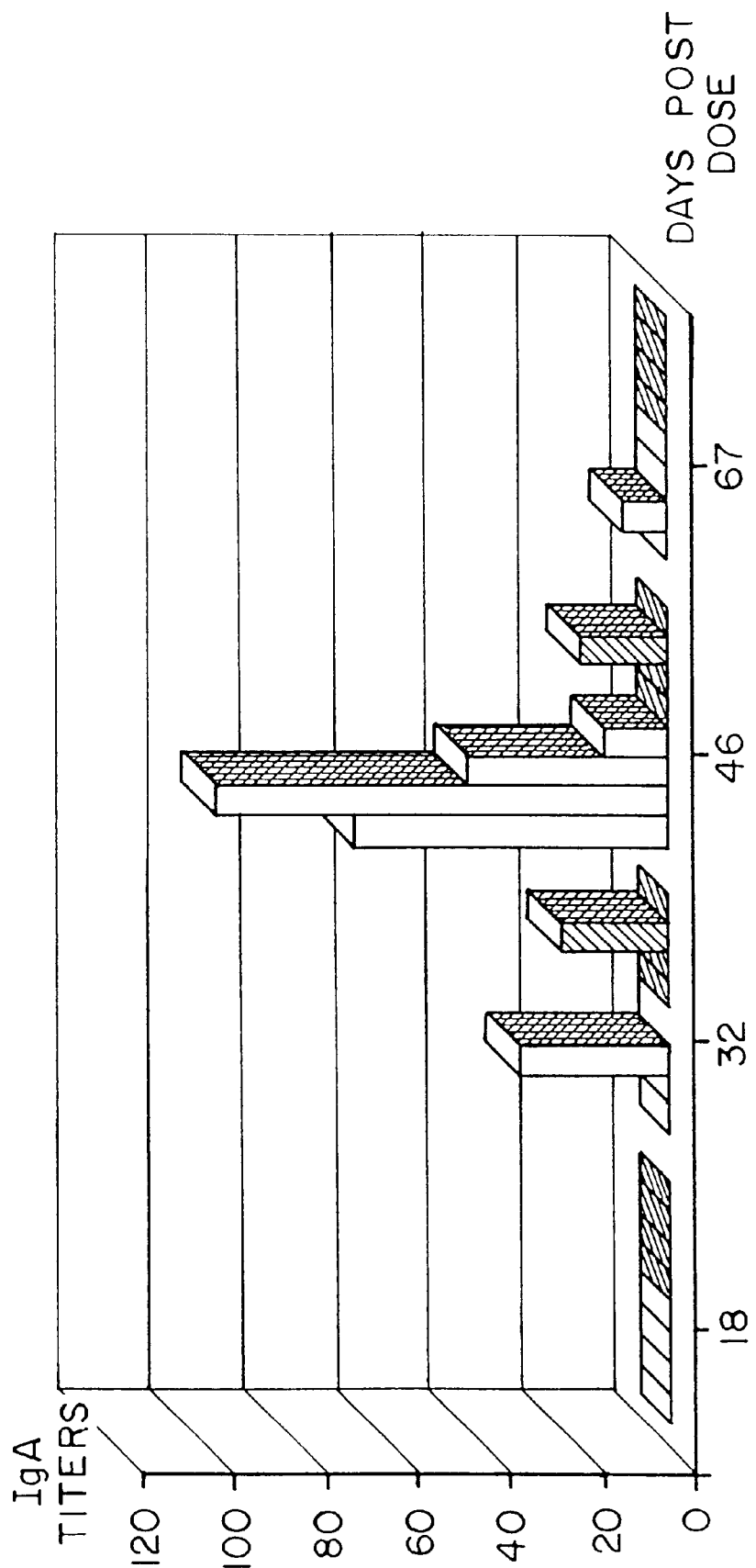
FIG. 1 is a graphic illustration of IgA response in mice dosed by oral gavage with ovalbumin (OVA) antigen, cholera toxin (CT) adjuvant, and modified amino acid carrier.

The present invention uses readily available and inexpensive carrier starting materials and provides a cost-effective method for preparing and isolating immunogenic compositions. The present invention is simple to practice and is amenable to industrial scale-up for commercial production.

The compositions of the subject invention are useful for administering antigens to any animals such as birds and mammals, including, but not limited to, primates and particularly humans. The compositions elicit an immunogenic response and provide immunization.

Antigens

Antigens suitable for use in the present invention include, but are not limited to, synthetic or naturally derived proteins and peptides, and particularly those which by themselves are unable to induce an efficient immune response or which induce tolerance; carbohydrates including, but not limited to, polysaccharides; lipopolysaccharides; and antigens isolated from biological sources such as, for example, microbes, viruses, or parasites, and subunits or extracts therefrom; or any combination thereof. Special mention is made of the antigens *Streptococcus pneumoniae, S. typhi* VI carbohydrate, *Hemophilus influenzae* (type B), Acellular *B. pertussis, Neisseria meningiditis* (A,C), *H. influenzae* (type B, Hib), *Clostridium tetani* (tetanus), *Corynebacterium diphtheriae* (diphtheria), and infectious bursal disease virus (IBDV) (attenuated and virulent).

Adjuvants

Adjuvants suitable for use in the present invention include, but are not limited to protein carriers such as protein containing appropriate T-cell epitopes; hydrophobic-antigens such as proteins with a lipid tail or antigens in oil with added MDP; polyclonal activators of T-cells such as PPD, poly A and poly U; B-cell activators such as antigen-polymerizing factors and B-cell mitogens; macrophage (APC) stimulators such as muramyl dipeptides (MDP) and derivatives thereof; and lipopolysaccharides (LPS); alternate pathway complement activators such as, for example, inulin, zymosan, endotoxin, levamisole, C. parvum; or any combinations thereof. Other useful adjuvants include lipoidal amines in general; polyphophazens; bacterial toxins such as *E. coli* heat labile enterotoxin (LT-OA), cholera or diphtheria toxin or subunits, thereof, such as, for example, cholera toxin β-subunit or *E. coli* heat labile anterotoxin β-subunit; bacterial toxoids; poly or di-saccharides; or any combination thereof such as, for example, cholera toxin and cholera toxin β-subunit.

Preferred adjuvants are mucosal adjuvants.

Carriers

The carriers of the present invention are modified amino acids; polyamino acids; or peptides or salts thereof. Modified amino acids, poly amino acids, or peptides are either acylated or sulfonated and include amino acid amides and sulfonamides.

Amino acids are the basic materials used to prepare these carriers. An amino acid is any carboxylic acid having at least one free amine group and includes naturally occurring and synthetic amino acids. The preferred amino acids for use in the present invention are -amino acids, and most preferably are naturally occurring -amino acids. Many amino acids and amino acid esters are readily available from a number of commercial sources such as Aldrich Chemical Co. (Milwaukee, Wis., USA); Sigma Chemical Co. (St. Louis, Mo., USA); and Fluka Chemical Corp. (Ronkonkoma, N.Y., USA).

Representative, but not limiting, amino acids suitable for use in the present invention are generally of the formula

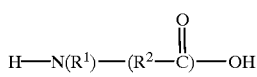

I wherein:

R$^1$ is hydrogen, C$_1$–C$_4$ alkyl, or C$_2$–C$_4$ alkenyl;

R$^2$ is C$_1$–C$_{24}$ alkyl, C$_2$–C$_{24}$ alkenyl, C$_3$–C$_{10}$ cycloalkyl, C$_3$–C$_{10}$ cycloalkenyl, phenyl, naphthyl, (C$_1$–C$_{10}$ alkyl) phenyl, (C$_2$–C$_{10}$ alkenyl) phenyl, (C$_1$–C$_{10}$ alkyl) naphthyl, (C$_2$–C$_{10}$ alkenyl) naphthyl, phenyl (C$_1$–C$_{10}$ alkyl), phenyl (C$_2$–C$_{10}$ alkenyl), naphthyl (C$_1$–C$_{10}$ alkyl), or naphthyl (C$_2$–C$_{10}$ alkenyl);

R$^2$ being optionally substituted with C$_1$–C$_4$ alkyl, C$_2$–C$_4$ alkenyl, C$_1$–C$_4$ alkoxy, —OH, —SH, —CO$_2$R$^3$, C$_3$–C$_{10}$ cycloalkyl, C$_3$–C$_{10}$ cycloalkenyl, heterocyclic having 3–10 ring atoms wherein the hetero atom is one or more of N, O, S, or any combination thereof, aryl, (C$_1$–C$_{10}$ alk)aryl, aryl(C$_1$–C$_{10}$ alkyl) or any combination thereof;

R$^2$ being optionally interrupted by oxygen, nitrogen, sulfur, or any combination thereof; and R$^3$ is hydrogen, C$_1$–C$_4$ alkyl, or C$_2$–C$_4$ alkenyl.

The preferred naturally occurring amino acids for use in the present invention as amino acids or components of a peptide are alanine, arginine, asparagine, aspartic acid, citrulline, cysteine, cystine, glutamine, glycine, histidine, isoleucine, leucine, lysine, methionine, ornithine, phenylalanine, proline, serine, threonine, tryptophan, tyrosine, valine, hydroxy proline, γ-carboxyglutamate, phenylglycine, or O-phosphoserine. The preferred amino acids are arginine, leucine, lysine, phenylalanine, tyrosine, tryptophan, valine, and phenylglycine.

The preferred non-naturally occurring amino acids for use in the present invention are β-alanine, α-amino butyric acid, γ-amino butyric acid, γ-(aminophenyl) butyric acid, α-amino isobutyric acid, 6-aminocaproic acid, 7-amino heptanoic acid, β-aspartic acid, aminobenzoic acid, aminophenyl acetic acid, aminophenyl butyric acid, γ-glutamic acid, cysteine (ACM), ε-lysine, ε-lysine, methionine sulfone, norleucine, norvaline, ornithine, d-ornithine, p-nitrophenylalanine, hydroxy proline, 1,2,3,4,-tetrahydroisoquinoline-3-carboxylic acid and thioproline.

Poly amino acids are either peptides or two or more amino acids linked by a bond formed by other groups which can be linked, e.g., an ester, anhydride or an anhydride linkage. One or more of the amino acids of a polyamino acid or peptide may be modified. Special mention is made of non-naturally occurring poly amino acids and particularly non-naturally occurring hetero-poly amino acids, i.e., of mixed amino acids.

Peptides are two or more amino acids joined by a peptide bond. Peptides can vary in length from dipeptides with two amino acids to polypeptides with several hundred amino acids. See, Walker, *Chambers Biological Dictionary*, Cambridge, England: Chambers Cambridge, 1989, page 215. Special mention is made of non-naturally occurring peptides and particularly non-naturally occurring peptides of mixed amino acids. Special mention is also made of dipeptides, tripeptides, tetrapeptides, and pentapeptides and particularly, the preferred peptides are dipeptides and tripeptides. Peptides can be homo- or hetero-peptides and can include natural amino acids, synthetic amino acids, or any combination thereof.

Acylated Amino Acid Carriers

Although the present invention encompasses any of the amino acids discussed above which have been acyclated, one group of preferred acylated amino acids have the formula Ar—Y—(R$^4$)$_n$—OH  II wherein Ar is a substituted or unsubstituted phenyl or naphthyl;

Y is

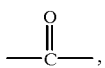

R$^4$ has the formula

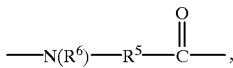

wherein:

R$^5$ is C$_1$ to C$_{24}$ alkyl, C$_1$ to C$_{24}$ alkenyl, phenyl, naphthyl, (C$_1$ to C$_{10}$ alkyl) phenyl, (C$_1$ to C$_{10}$ alkenyl) phenyl, (C$_1$ to C$_{10}$ alkyl) naphthyl, (C$_1$ to C$_{10}$ alkenyl) naphthyl, phenyl (C$_1$ to C$_{10}$ alkyl), phenyl (C$_1$ to C$_{10}$ alkenyl), naphthyl (C$_1$ to C$_{10}$ alkyl) and naphthyl (C$_1$ to C$_{10}$ alkenyl);

$R^5$ is optionally substituted with $C_1$ to $C_4$ alkyl, $C_1$ to $C_4$ alkenyl, $C_1$ to $C_4$ alkoxy, —OH, —SH and —$CO_2R^7$, cycloalkyl, cycloalkenyl, heterocyclic alkyl, alkaryl, heteroaryl, heteroalkaryl, halogens, or any combination thereof;

$R^7$ is hydrogen, $C_1$ to $C_4$ alkyl or $C_1$ to $C_4$ alkenyl;

$R^5$ is optionally interrupted by oxygen, nitrogen, sulfur or any combination thereof; and $R^6$ is hydrogen, $C_1$ to $C_4$ alkyl or $C_1$ to $C_4$ alkenyl.

Another group of preferred acylated amino acids have the formula

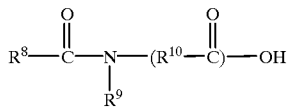

III wherein:

$R^8$ is (i) $C_3$–$C_{10}$ cycloalkyl, optionally substituted with $C_1$–$C_7$ alkyl, $C_2$–$C_7$ alkenyl, $C_1$–$C_7$ alkoxy, hydroxy, phenyl, phenoxy or —$CO_2R^{11}$, wherein $R^{11}$ is hydrogen, $C_1$–$C_4$ alkyl, or $C_2$–$C_4$ alkenyl; or (ii) $C_1$–$C_6$ alkyl substituted with $C_3$–$C_{10}$ cycloalkyl;

$R^9$ is hydrogen, $C_1$–$C_{24}$ alkyl, or $C_2$–$C_{24}$ alkenyl;

$R^{10}$ is $C_1$–$C_{24}$ alkyl, $C_2$–$C_{24}$ alkenyl, $C_3$–$C_{10}$ cycloalkyl, $C_3$–$C_{10}$ cycloalkenyl, phenyl, naphthyl, ($C_1$–$C_{10}$ alkyl) phenyl, ($C_2$–$C_{10}$ alkenyl) phenyl, ($C_1$–$C_{10}$ alkyl) naphthyl, ($C_2$–$C_{10}$ alkenyl) naphthyl, phenyl ($C_1$–$C_{10}$ alkyl), phenyl ($C_2$–$C_{10}$ alkenyl), naphthyl ($C_1$–$C_{10}$ alkyl) or naphthyl ($C_2$–$C_{10}$ alkenyl);

$R^{10}$ being optionally substituted with $C_1$–$C_4$ alkyl, $C_2$–$C_4$ alkenyl, $C_1$–$C_4$ alkoxy, —OH, —SH, —$CO_2R^{12}$, $C_3$–$C_{10}$ cycloalkyl, $C_3$–$C_{10}$ cycloalkenyl, heterocyclic having 3–10 ring atoms wherein the hetero atom is one or more of N, O, S or any combination thereof, aryl, ($C_1$–$C_{10}$ alk)aryl, aryl($C_1$–$C_{10}$ alkyl), halogens, or any combination thereof;

$R^{10}$ being optionally interrupted by oxygen, nitrogen, sulfur, or any combination thereof; and $R^{12}$ is hydrogen, $C_1$–$C_4$ alkyl, or $C_2$–$C_4$ alkenyl.

Special mention is made of salicyloyl phenylalanine, and the compounds having the formulas:

IV

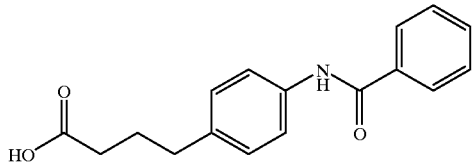

V

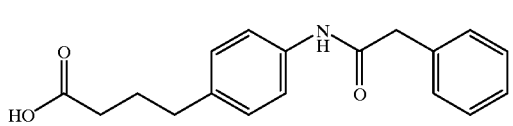

VI

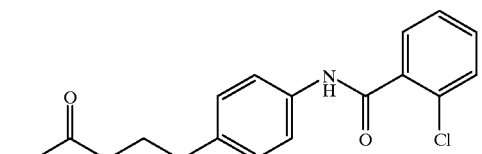

VII

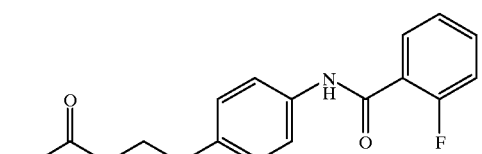

VIII

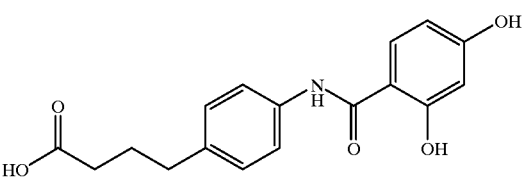

IX

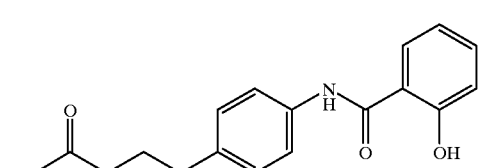

X

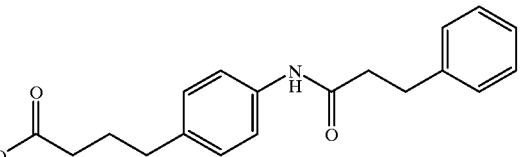

XI

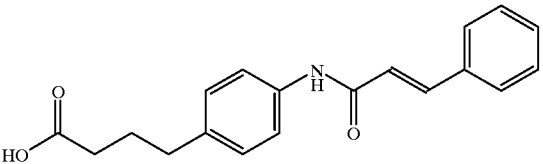

XII

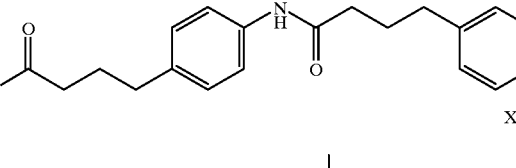

XIII

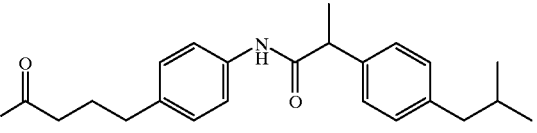

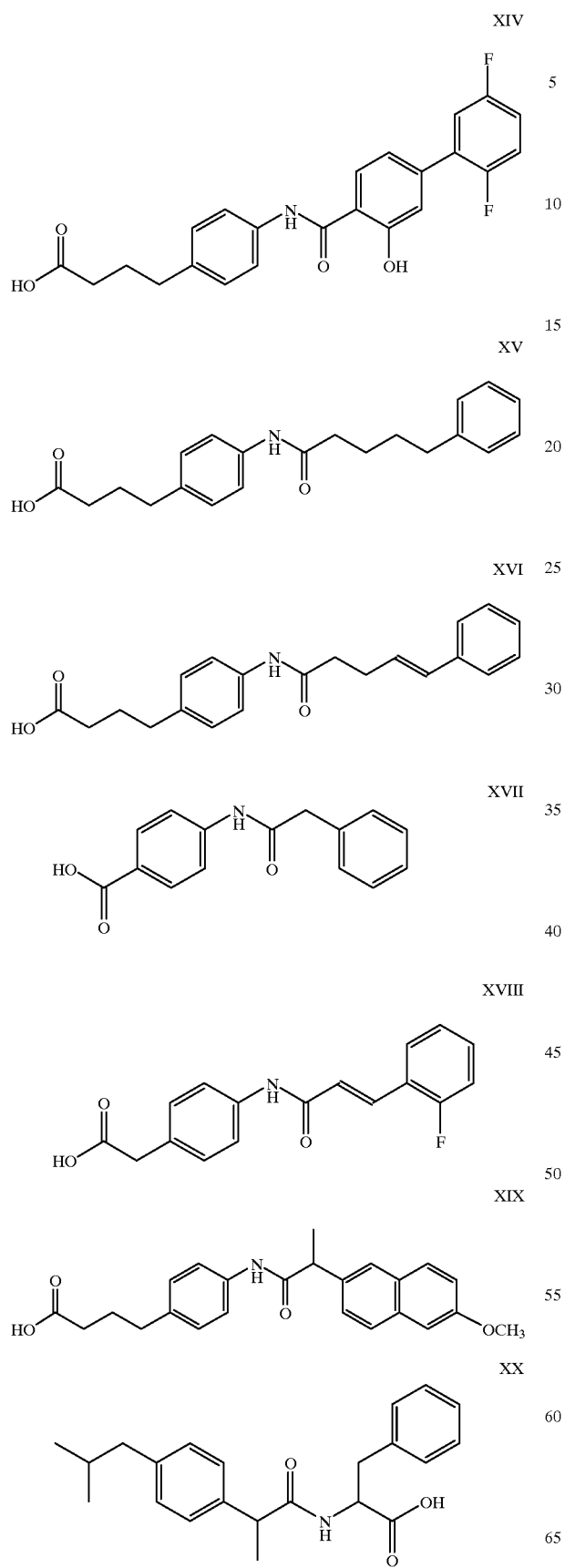

XXX
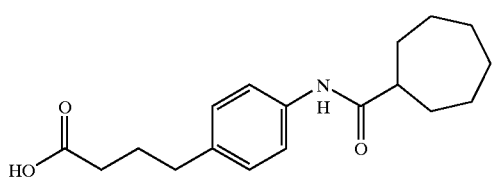
XXXI
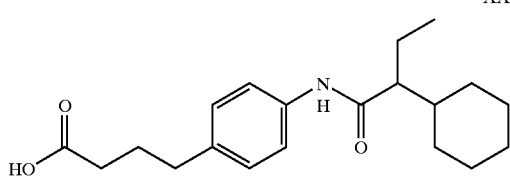
XXXII
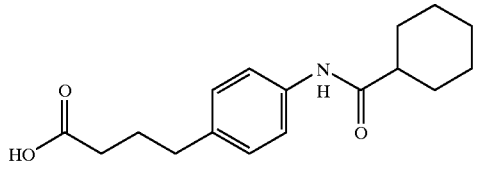
XXXIII
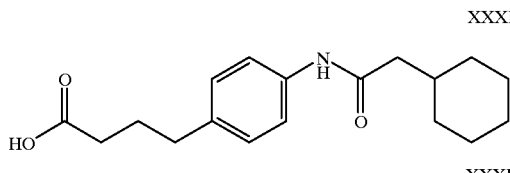
XXXIV
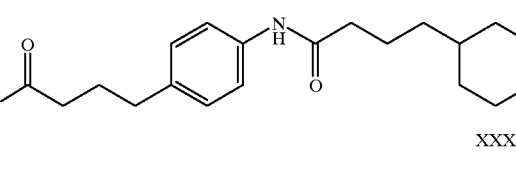
XXXV
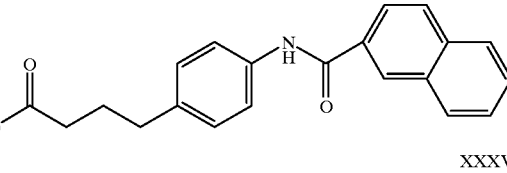
XXXVI
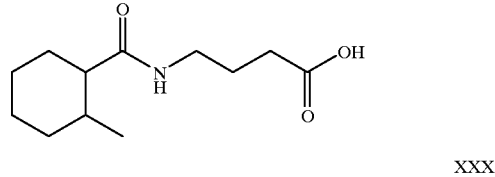
XXXVII
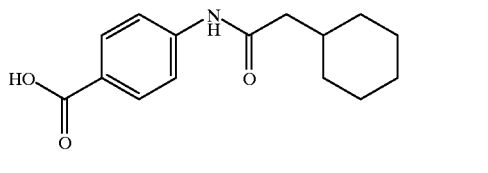
XXXVIII
XXXIX
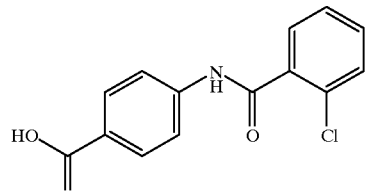
XL
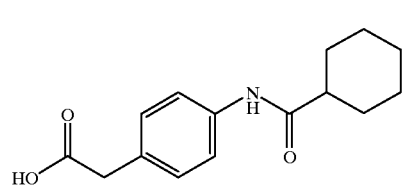
XLI
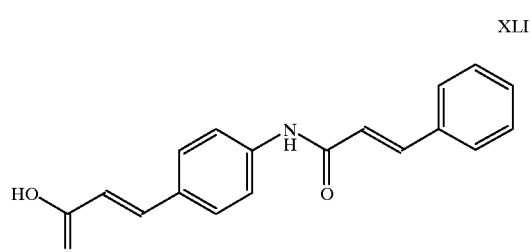
XLII
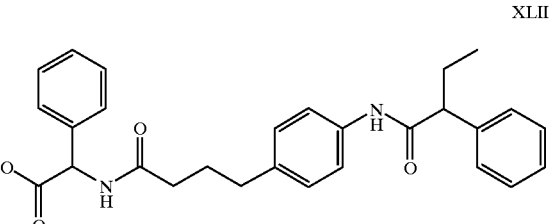
XLIII
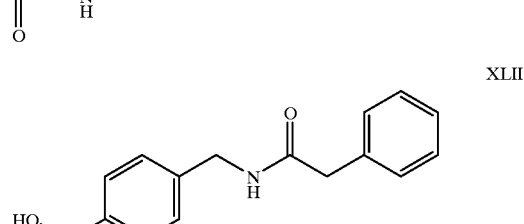
XLIV
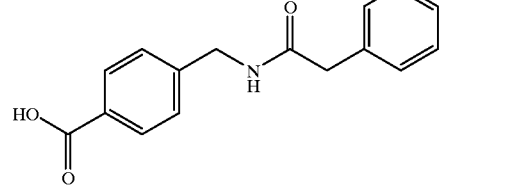
XLV
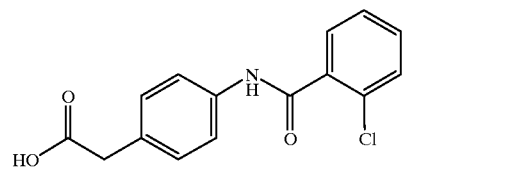

-continued

XLVI

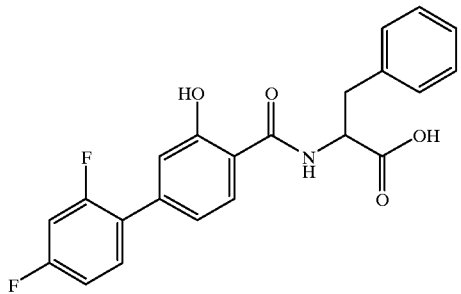

Special mention is also made of compounds having the formula:

XLVII

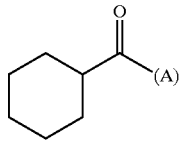

wherein A is Tyr, Leu, Arg, Trp, Phe, Lys, Val, or Cit; and
optionally wherein if A is Tyr, Arg, Trp, or Cit; A is acylated at 2 or more functional groups. Preferably A is Tyr; A is Tyr and is acylated at 2 functional groups; A is Leu; A is Arg; A is Arg and is acylated at 2 functional groups; A is Trp; A is Trp and is acylated at 2 functional groups; A is Cit; and A is Cit and is acylated at 2 functional groups.

Special mention is also made of compounds having the formula:

XLVIII

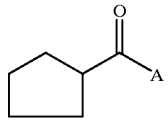

wherein A is Arg or Leu; and
wherein if A is Arg, A is optionally acylated at 2 or more functional groups;

XLIX

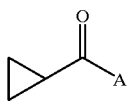

where A is Leu or phenylglycine;

L

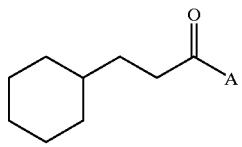

wherein A is phenylglycine; and

LI

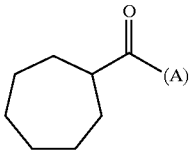

wherein A is phenylglycine.

Acylated amino acids may be prepared by reacting single amino acids, mixtures of two or more amino acids, or amino acid esters with an amine modifying agent which reacts with free amino moieties present in the amino acids to form amides.

Suitable, but non-limiting, examples of acylating agents useful in preparing acylated amino acids include acid chloride acylating agents having the formula

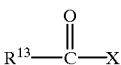

wherein:
$R^{13}$ is an appropriate group for the modified amino acid being prepared, such as, but not limited to, alkyl, alkenyl, cycloalkyl, or aromatic, and particularly methyl, ethyl, cyclohexyl, cyclopentyl, phenyl, or benzyl, and X is a leaving group. Typical leaving groups include, but are not limited to, halogens such as chlorine, bromine and iodine.

Examples of the acylating agents include, but are not limited to, acyl halides including, but not limited to, acetyl chloride, propionyl chloride, cyclohexanoyl chloride, cyclopentanoyl chloride, and cycloheptanoyl chloride, benzoyl chloride, hippuryl chloride and the like; and anhydrides, such as acetic anhydride, propionic anhydride, cyclohexanoic anhydride, benzoic anhydride, hippuric anhydride and the like. Preferred acylating agents include benzoyl chloride, hippuryl chloride, acetyl chloride, acetylsalicycloyl chloride, cyclohexanoyl chloride, cyclopentanoyl chloride, and cycloheptanoyl chloride.

The amine groups can also be modified by the reaction of a carboxylic acid with coupling agents such as the carbodiimide derivatives of amino acids, particularly hydrophilic amino acids such as phenylalanine, tryptophan, and tyrosine. Further examples include dicyclohexylcarbodiimide and the like.

If the amino acid is multifunctional, i.e., has more than one —OH, —NH$_2$ or —SH group, then it may optionally be acylated at one or more functional groups to form, for example, an ester, amide, or thioester linkage.

In the preparation of some acylated amino acids, the amino acids are dissolved in an aqueous alkaline solution of a metal hydroxide, e.g., sodium or potassium hydroxide and the acylating agent added. The reaction time can range from about 1 hour to about 4 hours, preferably about 2 to about 2.5 hours. The temperature of the mixture is maintained at a temperature generally ranging between about 5° C. and about 70° C., preferably between about 10° C. and about 50° C. The amount of alkali employed per equivalent of NH$_2$ groups in the amino acids generally ranges between about 1.25 moles and about 3 moles, and is preferably between about 1.5 moles and about 2.25 moles per equivalent of NH$_2$. The pH of the reaction solution generally ranges between about pH 8 and about pH 13, and is preferably between about pH 10 and about pH 12. The amount of amino modifying agent employed in relation to the quantity of amino acids is based on the moles of total free $NH_2$ in the amino acids. In general, the amino modifying agent is employed in an amount ranging between about 0.5 and about 2.5 mole equivalents, preferably between about 0.75 and about 1.25 equivalents, per molar equivalent of total $NH_2$ groups in the amino acids.

The modified amino acid formation reaction is quenched by adjusting the pH of the mixture with a suitable acid, e.g., concentrated hydrochloric acid, until the pH reaches between about 2 and about 3. The mixture separates on standing at room temperature to form a transparent upper layer and a white or off-white precipitate. The upper layer is discarded, and modified amino acids are collected by filtration or decantation. The crude modified amino acids are then mixed with water. Insoluble materials are removed by filtration and the filtrate is dried in vacuo. The yield of modified amino acids generally ranges between about 30 and about 60%, and usually about 45%. The present invention also contemplates amino acids which have been modified by multiple acylation, e.g., diacylation or triacylation.

If amino acid esters or amides are the starting materials, they are dissolved in a suitable organic solvent such as dimethylformamide or pyridine and are reacted with the amino modifying agent at a temperature ranging between about 5° C. and about 70° C., preferably about 25° C., for a period ranging between about 7 and about 24 hours. The amount of amino modifying agents used relative to the amino acid esters are the same as described above for amino acids.

Thereafter, the reaction solvent is removed under negative pressure and optionally the ester or amide functionality can be removed by hydrolyzing the modified amino acid ester with a suitable alkaline solution, e.g., 1 N sodium hydroxide, at a temperature ranging between about 50° C. and about 80° C., preferably about 70° C., for a period of time sufficient to hydrolyze off the ester group and form the modified amino acid having a free carboxyl group. The hydrolysis mixture is then cooled to room temperature and acidified, e.g., with an aqueous 25% hydrochloric acid solution, to a pH ranging between about 2 and about 2.5. The modified amino acid precipitates out of solution and is recovered by conventional means such as filtration or decantation.

The modified amino acids may be purified by acid precipitation, recrystallization or by fractionation on solid column supports. Fractionation may be performed on a suitable solid column supports, such as silica gel or alumina, using solvent mixtures such as acetic acid/butanol/water as the mobile phase; reverse phase column supports using trifluoroacetic acid/acetonitrile mixtures as the mobile phase; and ion exchange chromatography using water as the mobile phase. The modified amino acids may also be purified by extraction with a lower alcohol such as methanol, butanol, or isopropanol to remove impurities such as inorganic salts.

The modified amino acids generally are soluble in alkaline aqueous solution (pH≧9.0); partially soluble in ethanol, n-butanol and 1:1 (v/v) toluene/ethanol solution and insoluble in neutral water. The alkali metal salts, e.g., the sodium salts of the modified amino acids are generally soluble in water at about a pH of 6–8.

In a poly amino acid or peptide, one or more of the amino acids may be modified (acylated). Modified poly amino acids and peptides may include one or more acylated amino acid(s). Although linear modified poly amino acids and peptides will generally include only one acylated amino acid, other poly amino acid and peptide configurations can include more than one acylated amino acid. Poly amino acids and peptides can be polymerized with the acylated amino acid(s) or can be acylated after polymerization. Special mention is made of the compound:

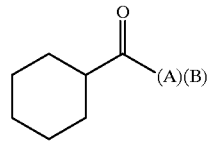

LII wherein A is Arg or Leu and B is Arg or Leu.

Sulfonated Amino Acid Carriers

Sulfonated modified amino acids, poly amino acids, and peptides are modified by sulfonating at least one free amine group with a sulfonating agent which reacts with at least one of the free amine groups present.

Special mention is made of compounds of the formula

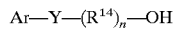

LIII wherein Ar is a substituted or unsubstituted phenyl or naphthyl;

Y is $-SO_2-$, $R^{14}$ has the formula

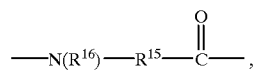

wherein:
$R^{15}$ is $C_1$ to $C_{24}$ alkyl, $C_1$ to $C_{24}$ alkenyl, phenyl, naphthyl, ($C_1$ to $C_{10}$ alkyl) phenyl, ($C_1$ to $C_{10}$ alkenyl) phenyl, ($C_1$ to $C_{10}$ alkyl) naphthyl, ($C_1$ to $C_{10}$ alkenyl) naphthyl, phenyl ($C_1$ to $C_{10}$ alkyl), phenyl ($C_1$ to $C_{10}$ alkenyl), naphthyl ($C_1$ to $C_{10}$ alkyl) and naphthyl ($C_1$ to $C_{10}$ alkenyl);

$R^{15}$ is optionally substituted with $C_1$ to $C_4$ alkyl, $C_1$ to $C_4$ alkenyl, $C_1$ to $C_4$ alkoxy, $-OH$, $-SH$ and $-CO_2R^{17}$ or any combination thereof;

$R^{17}$ is hydrogen, $C_1$ to $C_4$ alkyl or $C_1$ to $C_4$ alkenyl;

$R^{15}$ is optionally interrupted by oxygen, nitrogen, sulfur or any combination thereof; and $R^{16}$ is hydrogen, $C_1$ to $C_4$ alkyl or $C_1$ to $C_4$ alkenyl.

Suitable, but non-limiting, examples of sulfonating agents useful in preparing sulfonated amino acids include sulfonating agents having the formula $R^{18}-SO_2-X$ wherein $R^{18}$ is an appropriate group for the modified amino acid being prepared, such as, but not limited to, alkyl, alkenyl, cycloalkyl, or aromatics and X is a leaving group as described above. One example of a sulfonating agent is benzene sulfonyl chloride.

Modified poly amino acids and peptides may include one or more sulfonated amino acid(s). Although linear modified poly amino acids and peptides used generally include only one sulfonated amino acid, other poly amino acid and peptide configurations can include more than one sulfonated amino acid. Poly amino acids and peptides can be polymerized with the sulfonated amino acid(s) or can be sulfonated after polymerization.

Systems

Delivery of an antigen with an adjuvant and a carrier as described herein results in enhanced immune responses.

Another advantage of the present invention is that smaller amounts of antigen and/or adjuvant may be used to achieve an appropriate response. This latter advantage is particularly evident when the composition is in microsphere form.

In one embodiment of the present invention, the modified amino acids, poly amino acids, peptides, or salts may be used as a carrier by simply mixing one or more modified amino acids, poly amino acids, or peptides, or salts with the antigen and adjuvant prior to administration. In another embodiment, the modified amino acids may be used to form microspheres containing the antigen and adjuvant.

Microspheres containing antigen and adjuvant can generally be of the matrix form or the microcapsule form. The matrix form includes both a hollow matrix sphere in which the carrier forms a matrix shell-around a hollow center with the antigen and adjuvant distributed throughout the matrix and a solid matrix sphere in which the carrier forms a spherical matrix continuum in which the antigen and adjuvant are distributed.

The microcapsule form is one in which the encapsulated antigen and adjuvant independently are either in solution or are solid, with the carrier forming a shell around the encapsulated material. The microcapsule form is the form most often taken by the self assembly of the carriers of the present invention.

If the delivery composition is to be of the microsphere form, carrier microspheres can be prepared by dissolving the carrier in an appropriate solute and then stimulating self assembly by contacting the carrier solution with a precipitator. Solubility of the carrier can be regulated by the selection of the appropriate amino acids.

Furthermore, the microsphere carriers and, therefore, the compositions of the present invention can be pH adapted to be selectively soluble in specific acidic, basic, or neutral pH ranges.

Compositions which are targeted to an acidic environment can be made selectively soluble at acidic pH, such as the pH in the stomach. These compositions are prepared with an acid-soluble carrier. The acid-soluble carrier exists largely in the cation form in at least a portion of the pH range from about 1 to about 6.8. However, above about 6.8 or at selected ranges above pH 6.8, the carrier is largely unprotonated and insoluble in water. Therefore, the carrier could self assemble to microspheres at basic or neutral pH, and the antigen in the delivery composition would not be released until the carrier solubilizes upon encountering an acidic pH.

Compositions which are to be targeted to an alkaline environment can be made selectively soluble at alkaline pH, such as the pH in the distal portion of the intestine. These compositions are prepared with a base-soluble carrier. The base-soluble carrier exists largely in an anionic form in at least a portion of the pH range of from about 7.2 to about 11. However, below and at pH 7.2, the carrier is largely protonated and insoluble in water. Therefore, the carrier could self assemble to microspheres at acidic or neutral pH, and the antigen in the delivery composition would not be released until the carrier solubilizes upon encountering a basic pH.

Compositions which are targeted to a neutral environment can be made selectively soluble at neutral pH. These compositions are prepared with a neutral-soluble carrier. The neutral-soluble carrier exists largely in a neutral form at neutral pH, i.e. from about 6.8 to about 7.2. However, above or below this range, the carrier is insoluble in water. Therefore, the carrier could self assemble to microspheres at acidic or basic pH, and the antigen in the delivery composition would not be released until the carrier solubilizes upon encountering a neutral pH.

In a typical formulation, the final solution can contain from about 10 mg to about 2000 mg of carrier per ml of solution, preferably between about 75 to about 500 mg of carrier per ml of solution, and most preferably from about 75 to about 200 mg per ml. Optionally, the mixture is heated to a temperature between about 20° C. and about 60° C., preferably about 40° C., until the carrier dissolves. Particulates remaining in the solution may be filtered out by conventional means such as gravity filtration through filter paper. The carrier solution usually is maintained at the elevated temperature and is mixed with the antigen and/or adjuvant and a precipitator, for example, an acid solution such as, for example, aqueous acetic or citric acid at a concentration ranging from about 1 N to about 3 N for acid insoluble carriers, a basic solution for base insoluble carriers, and a neutralizing solution for neutral insoluble carriers. The antigen and/or adjuvant can be mixed with the precipitating solution or can be used separately. The resultant mixture is maintained for a period of time sufficient for microsphere formation as observed by light microscopy. Although it is preferred that the precipitating solution is added to the carrier solution, the carrier solution can be added to the precipitating solution as well.

The solutions above may optionally contain additives such as stabilizing additives. The presence of such additives promotes the stability and dispersability of the active agent in solution. The stabilizing additives may be employed at a concentration ranging between about 0.1 and 5 (w/v), preferably about 0.5% (w/v). Suitable, but non-limiting examples of stabilizing additives include buffer salts, gum acacia, gelatin, methyl cellulose, polyethylene glycol, polylysine, carboxylic acids, carboxylic acid salts, and cyclodextrins. The preferred stabilizing agents are gum acacia, gelatin, and methyl cellulose.

The amounts of antigen and adjuvant which may be encapsulated by the microsphere is dependent upon a number of factors which include the concentrations of antigen and adjuvant in the encapsulating solution as well as their affinities for the carrier. The concentrations of antigen and adjuvant in the final formulation also will vary depending on the required dosage for treatment. When necessary, the exact concentrations can be determined by, for example, reverse phase HPLC analysis.

When the present compositions are in microsphere form, the particle size of the microsphere can also aid in providing efficient delivery of the antigen to the target. Typically, microspheres of the present invention will have a diameter of less than 10 $\mu$m, preferably in the range of from about 0.1 $\mu$m to about 10 $\mu$m, and most preferably in the range of from 0.2 $\mu$m to about 10 $\mu$m. The size of the microspheres containing an antigen can be controlled by manipulating a variety of physical or chemical parameters, such as the pH, osmolarity, ionic strength of the encapsulating solution, or size of the ions in solution, and/or by the choice of the precipitator used in the microsphere forming and loading process.

For example, in the GI tract, it is often desirable to use microspheres which are sufficiently small to deliver effectively the antigen to the targeted area within the gastrointestinal tract. Small microspheres can also be administered parenterally by suspending the spheres in an appropriate fluid (e.g. isotonic solution) and injecting the solution directly into the circulatory system intramuscularly or subcutaneously. The mode of administration of the delivery compositions will vary, of course, depending upon the requirement of the antigen administered. It has been noted that large amino acid microspheres (greater than 50 $\mu$m) tend to be less effective as oral delivery systems.

The compositions of the present invention may also include one or more enzyme inhibitors. Such enzyme inhibitors include, but are not limited to, compounds such as actinonin or epiactinonin and derivatives thereof. These compounds have the formulas below:

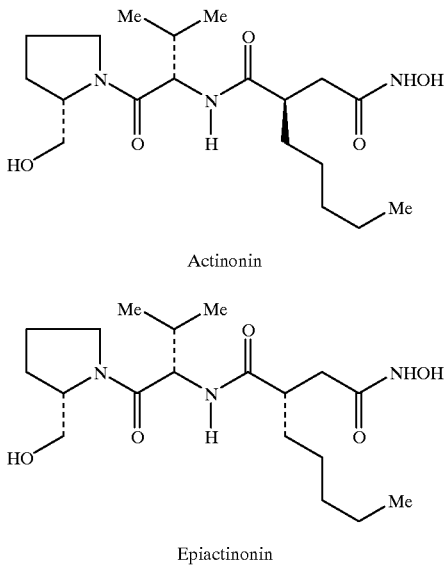

Actinonin

Epiactinonin

Derivatives of these compounds are disclosed in U.S. Pat. No. 5,206,384.

Actinonin derivatives have the formula:

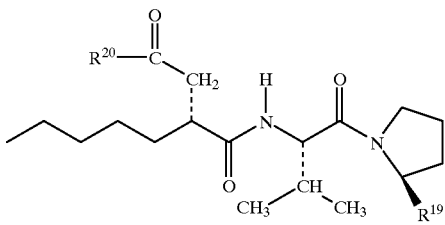

wherein $R^{19}$ is sulfoxymethyl or carboxyl or a substituted carboxyl group selected from carboxamide, hydroxyaminocarbonyl and alkoxycarbonyl groups; and $R^{20}$ is hydroxyl, alkoxy, hydroxyamino or sulfoxyamino group. Other enzyme inhibitors include, but are not limited to, aprotinin (Trasylol) and Bowman-Birk inhibitor.

The compositions of the present invention may be formulated into dosage units by the addition of one or more excipient(s), diluent(s), disintegrant(s), lubricant(s), plasticizer(s), colorant(s), or dosing vehicle(s). Preferred dosage unit forms are oral dosage unit forms. Most preferred dosage unit forms include, but are not limited to, tablets, capsules, or liquids. The dosage unit forms can include biologically or immunogenically effective amounts of the antigen and an biologically or immunogenically assisting effective amount of the adjuvant but can include less than such an amount if multiple dosage unit forms are to be used to administer a total dosage of the antigen and adjuvant. Dosage unit forms are prepared by methods conventional in the art.

The carriers of the present invention do not alter the physiological and biological properties of the antigen or the adjuvant. Furthermore, the encapsulation process need not alter the structure of the antigen. Any antigen can be incorporated within the amino acid microspheres.

The compositions are particularly advantageous for oral immunization with antigens which otherwise would be destroyed or rendered less effective by conditions encountered within the body of the animal to which it is administered, before the microsphere reaches its target zone such as peptides or proteins, which, by themselves, do not pass or are not taken up in the gastro-intestinal mucosa and/or are susceptible to chemical cleavage by acids and enzymes in the gastrointestinal tract. Such antigens include those used to provide immunization against diseases including but not limited to, influenza, diphtheria, tetanus, measles, polio, hepatitis and the like. The compositions of the invention are more effective at inducing both mucosal and serum antibody responses than antigens which are administered without the carriers specified herein and adjuvants. The antigens are administered to a mammal for their biological effect, such as, for example as immune stimulators Administration of the present compositions or dosage unit forms preferably is oral or by intraduodenal injection.

EXAMPLES

The invention will now be illustrated in the following non-limiting examples which are illustrative of the invention but are not intended to limit the scope of the invention.

Example 1

Preparation Of O,N-Dicyclohexanoyl-(L)-Tyrosine (L)-Tyrosine (61.6 g., 0.34 mole) was dissolved in 190 mL of 2 N sodium hydroxide. Cyclohexanoyl chloride (49.32 mL, 0.34 mole) was added dropwise to the mixture. Additional aqueous 2 N sodium hydroxide was added, and the reaction mixture was allowed to stir at room temperature for 2 hours. The mixture was then acidified to pH 9.5 with aqueous (4:1) hydrochloric acid. A precipitate formed which was separated by vacuum filtration. The solids were dissolved in 2 N sodium hydroxide and dried by lyophilization to furnish 33.5 g of N,O-dicyclohexanoyl-(L)-tyrosine. The product was purified by column chromatography on silica gel using butanol/acetic acid/water as the eluent system. The pure product was a white solid.

Properties are listed below:

Mass Spectrum: M+23 m/e 314.

$^1$H NMR (300 MHz, DMSO-d6): d=6.8 (d, 2H); 6.4 (d,2H); 4.4 (m, 1H); 2.5 (ddd,2H); 2.0 (m,2H); 1.6 (m,10H); 1.2(m, 10H).

IR (KBr) cm-1: 3350, 2900, 2850, 1600, 1520, 1450, 1400, 1300.

Example 2

Preparation of N-Cyclohexanoyl-(L)-Tyrosine

Cyclohexanoyl chloride (7 mL, 47 mmole) was added dropwise to a stirred solution of dry pyridine (400 mL) and O-benzyltyrosine benzyl ester (25 g, 46.8 mmole). The reaction temperature was maintained at 0° C. throughout the addition. The reaction mixture was stirred for an additional 2 hours after the addition was complete. The reaction mixture was concentrated to dryness in vacuo to provide a solid material. The solid was washed with aqueous hydrochloric acid (1N, 4×400 mL). The residue was dissolved in ethyl acetate (300 mL), washed with aqueous hydrochloric acid (1N, 2×500 mL), aqueous sodium bicarbonate (2×300 mL), and dried over magnesium sulfate. Filtration, followed by concentration in vacuo, provided an oil which was dissolved in methanol/tetrahydrofuran (400 mL/70 mL) and was hydrogenated at atmospheric pressure and room temperature over 10% palladium on carbon (600 mg). The reaction mixture was filtered through Celite and concentrated in vacuo to provide a solid which was recrystallized from ethyl acetate/hexane. The crystals were collected to-provide the N-cyclohexanoyl-(L)-tyrosine (8.7 g, 64%) as a white solid.

NMR results are listed below:

$^1$H NMR (300 MHz, D$_2$O) δ6.9 (d, 2H, aromatic), 6.6 (d, 2H, aromatic), 4.25 (m, 1H, NHCHCOOH), 2.95 (m, 1H, CH$_2$), 2.7 (m, 1H, CH$_2$) 2.05 (m, 1H, NHC(O)CH), 1.5 (br. m, 5H, cyclohexyl), 1.05 (br. m, 5H, cyclohexyl).

Example 3

Preparation of N-Cyclohexanoyl-(L)-Leucine

Cyclohexanoyl chloride (32.7 mL, 232 mmole) was added dropwise to a solution of (L)-leucine (37 g, 282 mmole) in aqueous sodium hydroxide (500 mL, 2 N). During the course of this addition, the reaction temperature was maintained below 45° C. using an ice/water bath, as necessary. The pH was maintained at about 10 by the addition of aliquots of 14 N NaOH, as necessary. After the addition was complete, the reaction mixture was stirred for an additional 2 hours at room temperature. The resulting clear solution was adjusted to pH 2.5 by the dropwise addition of concentrated hydrochloric acid. The precipitate was collected by filtration, re-dissolved in a minimum amount of 12 N sodium hydroxide, and re-precipitated by dropwise addition of concentrated hydrochloric acid and filtered. The crude reaction product was a white solid and contained about 85% N-cyclohexanoyl leucine sodium salt, about 10% cyclohexane carboxylic acid sodium salt, and about 5 N-cyclohexanoylleucylleucine sodium salt, by weight. The solid was washed with dilute aqueous hydrochloric acid (750 mL, 0.1 N) to provide N-cyclohexanoyl-(L)-leucine as a white crystalline solid (52.6 g, 77%).

NMR results are listed below:

$^1$H NMR (300 MHz D$_2$O) δ4.2 (t, 1H, NHCHCOOH), 2.0 (m, 1H, cyclohexylmethine), 1.6 (m, 7H, ring CH$_2$, i-Bu CH$_2$ and CH), 1.3 (m, 6H, ring CH$_2$), 0.8 (dd,6H,CH$_3$).

Example 4

Preparation of N-Cyclohexanoyl-(L)-Arginine and N$_\alpha$,N$_\gamma$-Dicyclohexanoyl-(L)-Arginine (L)-Arginine (103.2 g., 0.6 mole) was dissolved in 600 mL of 2 N sodium hydroxide. Cyclohexanoyl chloride (87 mL, 0.6 mole) was added dropwise to the mixture. The reaction mixture was maintained at 50° C. for 2 hours. The mixture was then cooled to room temperature and acidified to pH 2.3 with aqueous (4:1) hydrochloric acid. The precipitate which formed was separated by decantation. The solids were dissolved in 2 N sodium hydroxide and dried by lyophilization to furnish 64.1 g of crude N-cyclohexanoyl-(L)-arginine. The product was purified by column chromatography on silica gel/using butanol/acetic acid/water as the eluent system. The products isolated were N-cyclohexanoyl-(L)-arginine and N$_\alpha$,N$_\gamma$-dicyclohexanoyl-(L)-arginine.

Properties are listed below:
N-cyclohexanoyl-(L)-arginine:
Mass Spectrum: M+1 m/e 285.
$^1$H NMR (300 MHz, DMSO-d6): ppm δ=8.75(br, 1H); 7.6 (br, 5H); 4.0 (m, 1H); 3.05 (m, 2H); 2.15 (m, 1H) 1.1–1.5 (br.m, 14H).

N$_\alpha$,N$_\gamma$-dicyclohexanoyl-(L)-arginine:
Mass Spectrum: M+1 m/e 395.
$^1$H NMR: (300 MHz, DMSO-d6): d=2.0 (m, 3H); 1.8–1.4 (br. m, 17H); 1.3–1.0 (br. m, 20H)

Example 5

Preparation of N-Cyclohexanoyl-(L)-Citrulline

L-Citrulline (35.2 g., 0.2 mole) was dissolved in 200 mL of 2 N sodium hydroxide. Cyclohexanoyl chloride (29 mL, 0.2 mole) was added dropwise to the mixture. The reaction mixture was maintained at about 25° C. for 1 hour. The mixture was then acidified to pH 2.6 with aqueous (4:1) hydrochloric acid. The precipitate which formed was separated by decantation. The solids were dissolved in 2 N sodium hydroxide to pH 6.5 and dried by lyophilization to furnish 44.2 g of N-cyclohexanoyl-(L)-citrulline. The product was a white solid.

Properties are listed below:
Mass Spectrum: M+23 m/e 308.
$^1$H NMR (300MHZ,DMSO-d6): d=4.1 (dd, 1H); 2.9 (t, 2H); 2.1 (m,2H); 1.6–1.2 (br.m, 14H).
IR (KBr) cm-1: 3400, 3300, 2950, 2850, 1700, 1650, 1600, 1450, 1400 cm-1.

Example 6

Preparation of N-Cyclopentanoyl-(L)-Arginine (L)-Arginine (32.8 g., 0.19 moles) was dissolved in 188 mL of 2 N sodium hydroxide. Cyclopentanoyl chloride (22.9 mL, 0.19 moles) was added dropwise to the mixture. The reaction mixture was maintained at about 25° C. for 2 hours. The mixture was then acidified to pH 1.5 with aqueous (4:1) hydrochloric acid. The precipitate which formed was separated by decantation. The solids were dissolved in 2 N sodium hydroxide to pH 7.5 and dried by lyophilization to furnish 67.4 g of N-cyclopentanoyl-(L)-arginine. The product was a white solid.

Properties are listed below:
Mass Spectrum: M+1 m/e 271.

Example 7

Preparation of 4-(4-Phenylsulfonamido) Phenylbutyric Acid 4-(4-Aminophenyl)butyric acid, (20 g 0.11 moles) was dissolved in 110 mL of aqueous 2 N sodium hydroxide solution. After stirring for about 5 minutes at room temperature, benzene sulfonyl chloride (14.2 mL, 0.11 moles) was added dropwise into the amino acid solution over a 15 minute period. After stirring for about 3 hours at room temperature the mixture was acidified to pH 2 by addition of hydrochloric acid. This furnished a light brown precipitate which was isolated by filtration. The precipitate was washed with warm water and dried. The yield of 4-(phenylsulfonamido)4-phenylbutyric acid was 24.3 g (69%). The melting point was 123–25° C.

Example 8

Preparation of 4-Phenylsulfonamidobenzoic Acid

Following the procedure of Example 7, 4-aminobenzoic acid was converted to 4-(phenylsulfonamido)benzoic acid.

Example 9

Preparations of 4-(4-Phenylsulfonamido) Phenylacetic Acid, 4-(4-Phenylsulfonamido) Hippuric Acid, and 4-(4-Phenylsulfon-Amidomethyl)Benzoic Acid Following the procedure of Example 7, 4-aminophenylacetic acid, 4-aminohippuric acid, and 4-aminomethylbenzoic acid were converted to 4-(4-phenylsulfonamido)phenylacetic acid, 4-(4-phenylsulfonamido)hippuric acid, and 4-(4-phenylsulfonamidomethyl)benzoic acid respectively.

If necessary, the sulfonated amino acids can be purified by recrystallization and/or chromatography.

Example 10

Reaction of Mixed Amino Acids with Benzene Sulfonyl Chloride

A mixture of sixteen amino acids were prepared prior to chemical modification. The constituents of the mixture are summarized in Table 1. 65 grams of the amino acid mixture (total concentration of [—$NH_2$] groups=0.61 moles) was dissolved in 760 mL of 1 N sodium hydroxide solution (0.7625 equivalents) at room temperature. After stirring for 20 minutes, benzene sulfonyl chloride (78 ml, 1 eq.) was added over a 20 minute period. The reaction mixture was then stirred for 2.5 hours, without heating. As some precipitation had occurred, additional NaOH solution (2 N) was added to the solution until it reached pH 9.3. The reaction mixture stirred overnight at room temperature. Thereafter, the mixture was acidified using dilute hydrochloric acid (38%, 1:4) and a cream colored material precipitated out. The resulting precipitate was isolated by decantation and dissolved in sodium hydroxide (2 N). This solution was then reduced in vacuo to give a yellow solid, which was dried on the lyophilizer.

TABLE 1

Amino Acid Composition

| Amino Acid | Weight (g) | % of Total Weight | No. of moles of each Amino Acid (×$10^{-2}$) | No. of Moles of -[-$NH_2$] |
|---|---|---|---|---|
| Thr | 2.47 | 3.8 | 2.07 | 2.07 |
| Ser | 2.25 | 3.46 | 2.1 | 2.1 |
| Ala | 4.61 | 7.1 | 5.17 | 5.17 |
| Val | 4.39 | 6.76 | 3.75 | 3.75 |
| Met | 0.53 | 0.82 | 0.35 | 0.35 |
| Ile | 2.47 | 3.8 | 0.36 | 0.36 |
| Leu | 3.86 | 5.94 | 2.95 | 2.95 |
| Tyr | 1.03 | 1.58 | 0.56 | 0.56 |
| Phe | 4.39 | 6.76 | 0.27 | 0.27 |
| His | 2.47 | 3.8 | 1.6 | 3.2 |
| Lys | 4.94 | 7.6 | 3.4 | 6.8 |
| Arg | 5.13 | 7.9 | 2.95 | 5.90 |
| Glutamine | 9.87 | 15.18 | 6.76 | 13.42 |
| Glutamic Acid | 9.87 | 15.18 | 6.70 | 6.70 |
| Asparagine | 3.32 | 5.11 | 2.51 | 5.02 |
| Aspartic Acid | 3.32 | 5.11 | 2.50 | 2.50 |

Example 11

Reaction of Five Mixed Amino Acids with Benzene Sulfonyl Chloride

An 86.1 g (0.85 moles of $NH_2$) mixture of amino acids (see Table 2) was dissolved in 643 mL (1.5 eq.) of aqueous 2 N sodium hydroxide solution. After stirring for 30 minutes at room temperature, benzene sulfonyl chloride (108 mL, 0.86 moles) was added portionwise into the amino acid solution over a 15 minute period. After stirring for 2.5 hours at room temperature, the pH of the reaction mixture (pH 5) was adjusted to pH 9 with additional 2 N sodium hydroxide solution. The reaction mixture stirred overnight at room temperature. Thereafter, the pH of the reaction mixture was adjusted to pH 2.5 by addition of dilute aqueous hydrochloric acid solution (4:1, $H_2O$:HCl) and a precipitate of modified amino acids formed. The upper layer was discarded and the resulting yellow precipitate was isolated by decantation, washed with water and dissolved in 2 N sodium hydroxide (2 N). The solution was reduced in vacuo to give a yellow solid which was lyophilized overnight. The yield of crude modified amino acid was 137.9 g.

Example 12

Reaction Of Five Mixed Amino Acids With Benzoyl Chloride

An 86 g (0.85 moles of $NH_2$) mixture of amino acids (see Table 2 in Example 11) was dissolved in 637 mL (1.5 eq.) of aqueous 2 N sodium hydroxide solution. After stirring for 10 minutes at room temperature, benzoyl chloride (99 mL, 0.85 moles) was added portionwise into the amino acid solution over a 10 minute period. After stirring for 2.5 hours at room temperature, the pH of the reaction mixture (pH 12) was adjusted to pH 2.5 using dilute hydrochloric acid (4:1, $H_2O$:HCl) and a precipitate of modified amino acids formed. After settling for 1 hour, the resulting precipitate was isolated by decantation, washed with water and dissolved in sodium hydroxide (2 N). This solution was then reduced in vacuo to give crude modified amino acids as a white solid (220.5 g).

TABLE 2

Amino Acid Composition

| Amino Acid | Moles of Amino Acid (×$10^{-2}$) | Moles of [-$NH_2$] × $10^{-2}$ |
|---|---|---|
| Valine | 7.5 | 7.5 |
| Leucine | 10.7 | 10.5 |
| Phenylalanine | 13.4 | 13.4 |
| Lysine | 21.0 | 42.0 |
| Arginine | 6.0 | 12.0 |

Example 13

Preparation of N-Phenylsulfonylvaline

L-Valine (50 g, 0.43 mole) was dissolved in 376 mL (0.75 eq.) of aqueous 2 N sodium hydroxide by stirring at room temperature for 10 minutes. Benzene sulfonyl chloride (68.7 mL, 0.38 mole, 1.25 eq.) was then added to the amino acid solution over a 20 minute period at room temperature. After stirring for 2 hours at room temperature, a precipitate appeared. The precipitate was dissolved by adding 200 mL of additional 2 N sodium hydroxide solution. After stirring for an additional 30 minutes, dilute aqueous hydrochloric acid solution (4:1, $H_2O$:HCl) was added until the pH of the reaction mixture reached 2.6. A precipitate of modified amino acid formed was recovered by decantation. This material was dissolved in 2 N sodium hydroxide and dried in vacuo to give a white solid. The yield of crude modified amino acid wad 84.6 g, 77%.

Example 14

Preparation of N-Hippurylphenylalanine

L-Phenylalanine methyl ester hydrochloride (15 g, 0.084 mole) was dissolved in dimethylformamide (DMF) (100 mL) and to this was added pyridine (30 mL). A solution of hippuryl chloride (16.6 g, 0084 moles in 100 mL DMF) was immediately added to the amino acid ester solution in two portions. The reaction mixture was stirred at room temperature overnight. The reaction mixture was then reduced in vacuo and dissolved in 1 N aqueous sodium hydroxide. The solution was heated at 70° C. for 3 hours in order to hydrolyze the methyl ester to a free carboxyl group. Thereafter, the solution was acidified to pH 2.25 using dilute aqueous hydrochloric acid solution (1:3 $HCl/H_2O$). A gum-like precipitate formed and this was recovered and dissolved in 1 N sodium hydroxide. The solution was reduced in vacuo to afford 18.6 g of crude modified amino acid product (Yield 18.6 g). After recrystallization from acetonitrile, pure modified phenylalanine (12 g) was recovered as a white powder. m.p. 223–225° C.

Example 15

Preparation Of Antigen/Delivery System

A carrier solution of 300 mg of the mixture of modified amino acids, prepared in Example 11, was added to 1.5 ml of water and mixed.

Cholera toxin (CT) adjuvant solution was prepared by reconstituting it in water at a concentration of 1 mg/ml.

Ovalbumin (3 mg) (OVA) antigen was dissolved in 1.2 ml of a solution of 1.7 N citric acid/1 gum acacia, and 0.3 ml of the cholera toxin solution was added.

The carrier solution and the OVA/CT solution were warmed to 40° C. and mixed together. The sample had a carrier concentration of 100 mg/mL and an OVA concentration of 1 mg/mL.

Example 16

Antigen in Vivo Experiments in Mice

Following the procedure in Example 15, a preparation of antigen (1 mg/ml of OVA), adjuvant (100 μg/ml of CT) with carrier (100 mg/ml of modified amino acid carrier) was prepared. Fasted mice were anesthetized with Ketamine, and administered, by oral gavage, a dose containing 100 μg OVA, 10μg CT, and 10 mg of carrier.

Intestinal secretions were collected on days 18, 32, 46, and 67 after dosing with the antigen/adjuvant/carrier preparation. The mice were dosed with a hypertonic solution prior to collection of the secretion samples. The secretions were then placed in a solution containing protease inhibitors. The resultant solution was cleared by centrifugation and assayed for total and OVA-specific IgA. IgA titer was determined by analyzing the secretions for the total IgA in the secretions and the OVA-specific IgA using the ELISA procedure below. The OVA-specific IgA could then be calculated from the results. IgA was expressed as "units" of specific anti-OVA IgA.

Elisa For Total IgA in Intestinal Secretions

1. Coat plate with 100 μl per well of affinity purified goat anti-mouse IgA (1μg/ml) in carbonate buffer (pH 9.6). Incubate overnight at 4° C.

2. Wash with an imidazole buffer having 0.05% Tween 20).

3. Add 1/10 diluted BSA blocking solution, 300 ml per well. Incubate, with shaking, 30 minutes at room temperature.

4. Wash with an imidazole buffer having 0.05% Tween 20.

5. Add 100 μl per well of serially diluted samples starting at 1/1000. Standard reference Mouse IgA is run at 6 dilutions: 1/150,000 (10 μl of Mouse IgA to 10 ml of buffer (1/1000). Add 100 μl of this solution to 14.9 ml of buffer (final dilution 1/150,000)) (16.32 ng/ml) (standard (1)); 200,000 3 ml of standard (1)+1 ml of buffer (1/200,000) (12.25 ng/ml) (standard (2)); 300,000 2 ml of standard (1)+2 ml of buffer (1/300,000) (8.16 ng/ml) (standard (3)); 400,000 2 ml of standard (2) +2 ml of buffer (1/400,000) (6.125 ng/ml) (standard (4)); 600,000 1 ml of standard (3)+1 ml of buffer (1/600,000) (4.08 ng/ml) (standard (5)); and 800,000 1 ml of standard (4)+1 ml of buffer (1/800,000) (3.06 ng/ml) (standard (6)). Incubate for one hour at room at room temperature, shaking at high speed.

6. Wash 8 times with an imidazole buffer having 0.05% Tween 20.

7. Add 100 μl per well of a 1/10,000 dilution of Rabbit anti-Mouse IgA in 1/15 diluent containing 4% PEG 6000. Mix briefly on shaker. Incubate overnight at 4° C.

8. Wash 8 times with an imidazole buffer having 0.05% Tween 20.

9. Add 100 μl per well of a 1/10,000 dilution of Alkaline-Phosphatase conjugated-Goat anti-Rabbit IgG in 1/15 diluent containing 4% PEG 6000. Incubate one hour at room temperature, with rapid shaking.

10. Wash 8 times with an imidazole buffer having 0.05% Tween 20.

11. Add 100 μl per well of PNPP/DEA, pH 9.8. Incubate 30 minutes at room temperature (so that maximum OD=1.8–2.0). Read OD 405, subtracting OD of appropriate background well.

12. Calculate total IgA in samples from standard curve (OD vs. log [IgA], taking the average of the values calculated for all dilutions whose OD's fall within the standard curve (i.e., find OD for sample which falls within the linear range of the curve and interpolate to find its concentration on the curve. Multiply this value by the appropriate dilution factor for that value).

Elisa for Specific Anti-OVA IgA in Intestinal Secretions

1. Coat plate with OVA. Add 100 μl of a 4 μg/ml solution of OVA in carbonate buffer (pH 9.6) to each well.

2. Incubate overnight at 4° C. or two hours at room temperature with rapid shaking.

3. Empty wells and wash 4 times with an imidazole buffer having 0.05 Tween 20.

4. Add 300 μl of BSA solution to each well and incubate 30 minutes at room temperature with shaking.

5. Wash 4 times with a imidazole buffer having 0.05% Tween 20.

6. Place intestinal secretion samples in 37° C. water bath until almost thawed, and centrifuge at 4° C. at 4000 rpm for 10 minutes to remove any precipitate.

7. Add 100 μl per well of appropriately diluted samples (three-fold serial dilutions from ½ up to 1/486).

Leave at least two "background" wells (all reagents except sample).

Negative control: pooled secretions collected from naive mice (diluted as with samples.)

Reference: Rabbit anti-OVA IgG diluted 1/200,000 2 wells)

8. Incubate one hour at room temperature with rapid shaking. 9. Wash 8 times with a imidazole buffer having 0.05% Tween 20.

10. (a) To secretions: Add 100μl of dilute (1/1000) Alkaline-Phosphatase conjugated anti-mouse IgA in 1/15 diluent containing 4% PEG 6000.

(b) To reference and one background well: 100 μl of 1/10,000 diluted A-P conjugated Goat anti-rabbit IgG in 1/15 diluent+4% PEG 6000.

11. Incubate one hour with rapid shaking.

12. Wash 8 times with an imidazole buffer having 0.05% Tween 20.

13. Add 100 μl of freshly prepared p-NPP substrate in diethanolamine buffer to each well.

14. Incubate 30 minutes at room temperature in the dark.

15. Read $OD_{405}$ subtracting the average OD of the appropriate background wells.

16. Define the number of "antibody units" in the sample as 1/dilution of the sample whose OD 405 average OD 405 of the IgG reference wells×100.

$$\text{Express } IgA \text{ content of samples as}: \frac{(\text{antibody units of specific } IgA)}{(\mu g \text{ total } IgA)}$$

Results are illustrated in FIG. 1.

Example 17

Antigen in Vivo Experiment

Following the procedure in Example 15, a composition containing antigen (1 mg/ml of OVA), adjuvant (100 μg/ml of CT) and carrier (100 mg/ml of cyclohexanoyl-Arg) was prepared. Mice were administered, by oral gavage, a dose containing 100 μg OVA, 10μg CT and 10 mg of carrier. Blood samples were taken at six weeks post dose. Serum was assayed using an ELISA to measure anti-OVA serum IgG. The procedure was as described below:

Serum IgG Titer Determination

1. Add 100 μl OVA solution (4μg/ml in carbonate buffer, pH 9.6) to each well.

2. Incubate at 4° C. overnight, or 2 hours at room temperature with shaking.

3. Empty and wash plate 4 times with imidazole buffer having 0.05% Tween 20 and one 5 minute soak.

4. Add 300 μl of BSA solution and incubate 30 minutes at room temperature.

5. Wash as above.

6. Add 100 ml of 1/15 diluted BSA solution to each well except first row of samples, first standard curve well, and wells for positive and negative controls.

7. Add samples and controls.

Samples: Place 150 μl of a 1/200 dilution of each sample in first well of sample rows.

Serially dilute 50 μl for 3-fold dilutions.

Positive Controls: Place 200 μl of hyper immune serum at 1/2000 dilution in first well. Serially dilute 100 μl two-fold to 1/64000 (6 wells).

Negative control: pooled serum from naive mice (1/200 dilution): 100 μl.

"Background": all reagents except serum in at least two wells.

8. Incubate two hours at room temperature with shaking.

9. Wash 8 times with imidazole buffer having 0.05% Tween 20 and one 5 minute soak.

10. Add 100 μl of Goat anti-Mouse IgG Alkaline Phosphatase Conjugate (diluted 1/1000 in 1/15 PBS/BSA solution containing 4% PEG 6000)

11. Incubate overnight at 4° C. after shaking for a few minutes.

12. Wash 8 times with imidazole buffer having 0.05% Tween 20.

13. Add 100 μl of freshly prepared pNPP solution to each well and develop at room temperature in the dark.

14. Read $OD_{405}$. (Subtract blank i.e., empty well, not background).

15. Record when $OD_{405}$ of 1/2000 standard=1.2 (about 0.5–1 hour).

16. Calculate antibody titers in samples by interpolation of OD's of dilutions. (max dilution at which $OD_{405}=3\times$ background).

Figure 2:
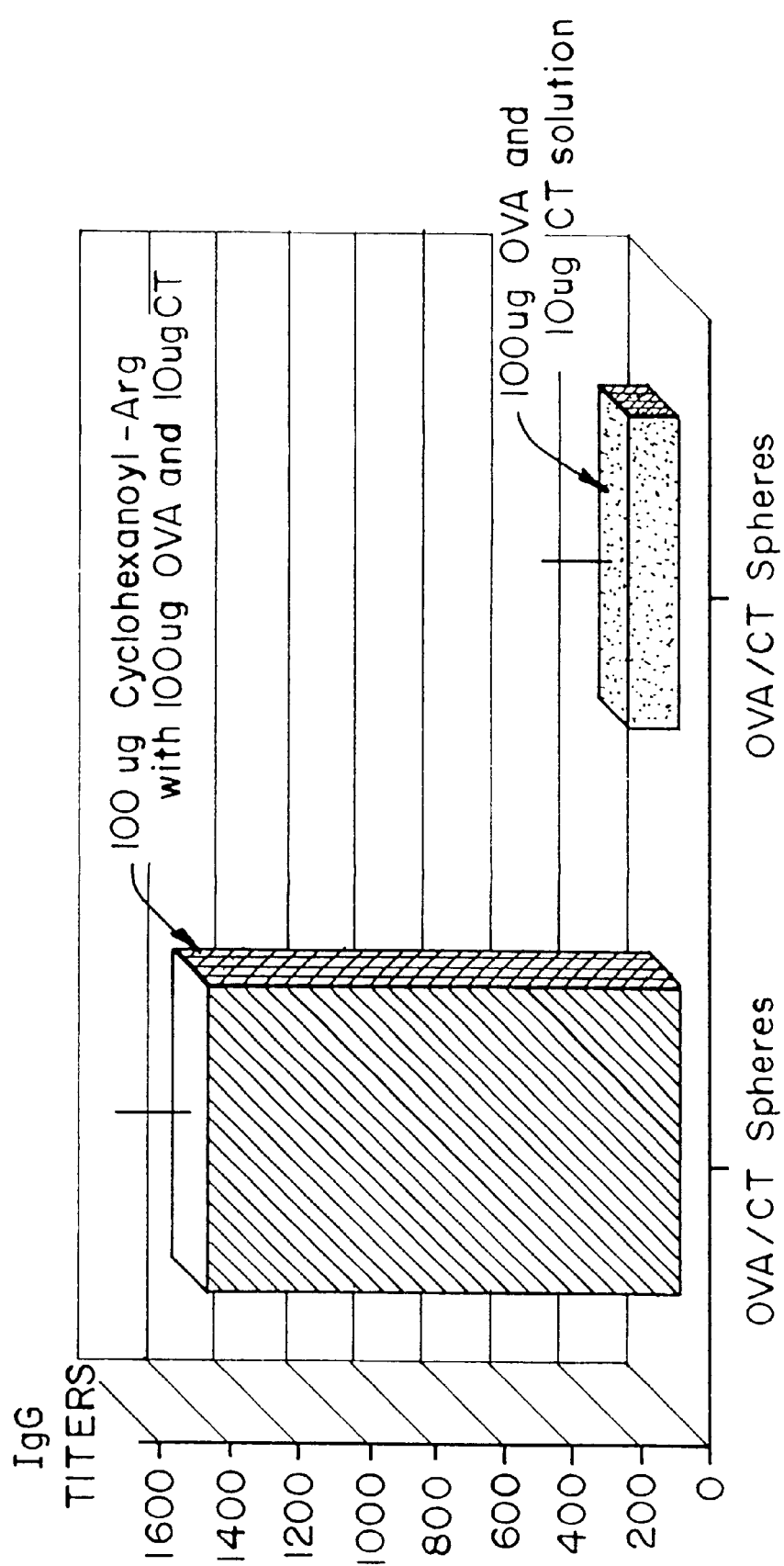
FIG. 2 is a graphic illustration of the induction of IgG titers in mice dosed by oral gavage with OVA antigen, CT adjuvant, and cyclohexanoyl-Arg carrier and of comparison testing in mice using OVA antigen and CT adjuvant without carrier.

Results are illustrated in FIG. 2.

Comparative Example 17A

Antigen in Vivo Experiment

A composition of antigen (OVA) and adjuvant (CT) was prepared. Mice were administered, by oral gavage, a dose containing antigen (100 μg OVA) and adjuvant (10 μg CT). Blood samples were collected and analyzed as described in Example 17.

Results are illustrated in FIG. 2.

Example 18

Antigen in Vivo Experiment

Following the procedure of Example 15, a composition of antigen (1 mg/ml of OVA), adjuvant (100 μg/ml of CT) and carrier (100 mg/ml of cyclohexanoyl-Arg) was prepared. Mice were administered, by oral gavage, a dose containing 100 μg of OVA, 10 μg of CT and 10 mg of carrier. Secretion samples were collected and analyzed at 46 days post dose as described in Example 16.

Figure 3:
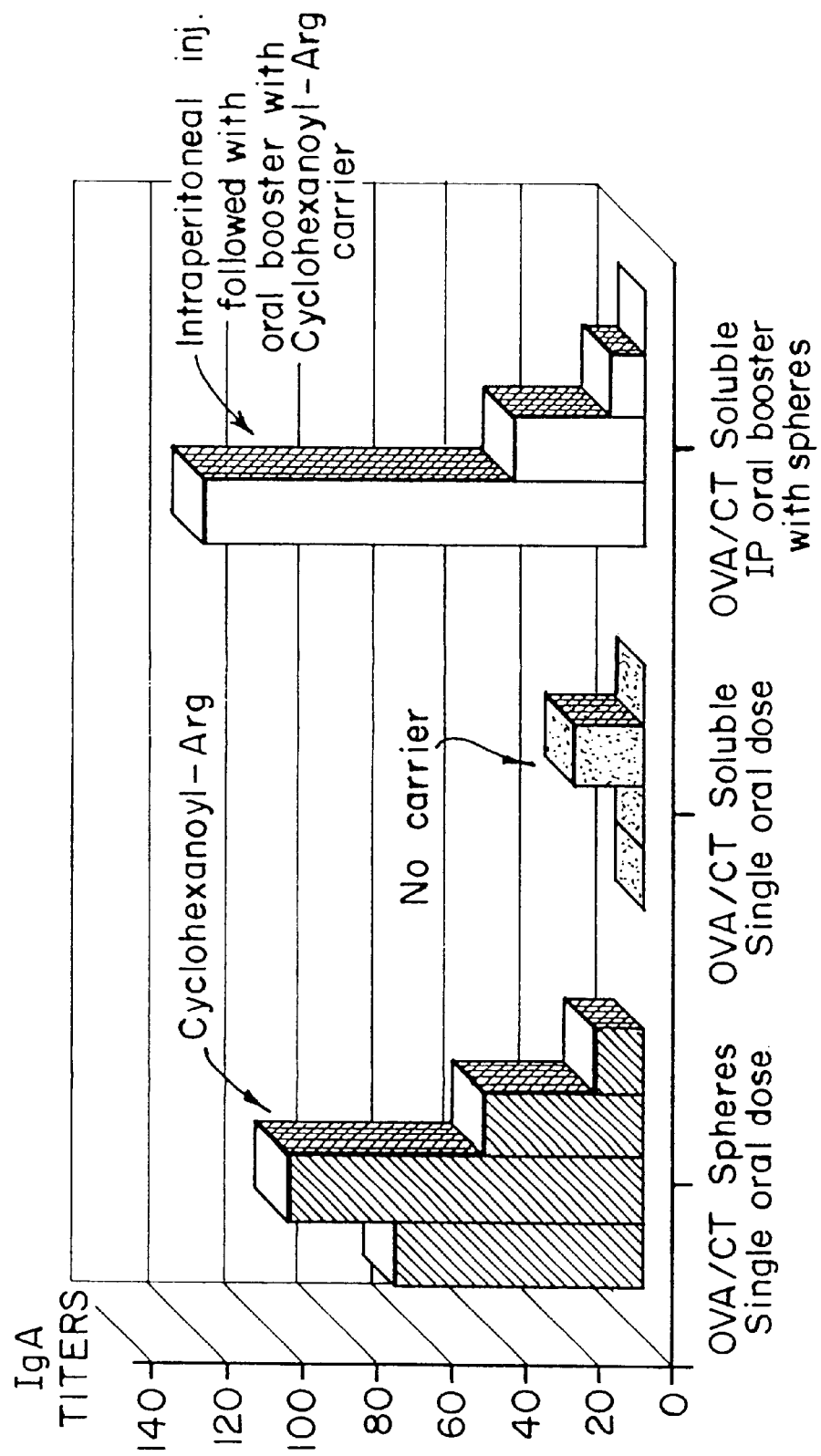
FIG. 3 is a graphic illustration of IgA titers in mice dosed by oral gavage with OVA antigen, CT adjuvant and cyclohexanoyl-Arg carrier or with intraperitoneal injection of OVA antigen and CT adjuvant followed by an oral booster of OVA antigen, CT adjuvant and cyclohexanoyl-Arg carrier in comparison to IgA titers in mice dosed by oral gavage with OVA antigen and CT adjuvant without carrier.

Results are illustrated in FIG. 3.

Comparative Example 18A

Antigen in Vivo Experiment

Following the procedure of comparative Example 17A mice were administered a composition containing antigen (100 μg OVA) and adjuvant (10g CT). Secretion samples were collected and analyzed at 46 days post dose as described in Example 16.

Results are illustrated in FIG. 3.

Example 19

Antigen in Vivo Experiment

Mice were administered, by intraperitoneal injection, an antigen preparation containing antigen (10 μg OVA) and adjuvant (10 μg CT). This was followed by a booster administered by oral gavage, containing antigen (100 μg OVA) adjuvant (10 μg CT) and 10 mg of cyclohexanoyl-Arg. Secretion samples were collected and analyzed at 46 days post dose as described in Example 16.

Results are illustrated in FIG. 3.

Example 20

Preparation of Antigen/Carrier Composition

A carrier solution is prepared by adding 90 mg of N-cyclohexanoyl-(L)-tyrosine and 135 mg of N-cyclohexanoyl-leucine to 1.5 ml of water.

Cholera toxin (CT) adjuvant solution is prepared by reconstituting CT in water at a concentration of 1 mg/ml.

Ovalbumin (3 mg) (OVA) antigen is dissolved in 1.2 ml of a solution of 1.7 N citric acid/1% gum acacia, and 0.3 ml of the cholera toxin solution is added.

The carrier solution and the OVA antigen/CT adjuvant solution are warmed to 40° C. and mixed together. The sample has a carrier concentration of 75 mg/mL, an OVA antigen concentration of 1 mg/mL, and an CT adjuvant concentration of 100 µg/mL.

Example 21

Antigen in Vivo Experiments in Mice

Fasted mice are anesthetized with Ketamine, and administered, by oral gavage, a dose of a composition prepared according to the method of Example 20, containing 100 µg OVA, 10 µg CT, and 7.5 mg of carrier.

Intestinal secretions were collected on days 18, 32, 46, and 67 after dosing with the antigen/adjuvant/carrier composition. The mice were dosed with a hypertonic solution prior to collection of the secretion samples. The secretions are then placed in a solution containing protease inhibitors. The resultant solution is cleared by centrifugation and is assayed for total and OVA-specific IgA's using the ELISA procedure described in Example 15. The OVA-specific IgA titer is calculated from the results.

Example 22

Immunization of Chickens

A solution containing formalin-inactivated Infectious Bursal Disease Virus (IBDV) (Maine Biological Laboratories, Winslowe, Me.) was prepared by diluting a buffered solution of IBDV ($2.5 \times 10^9$ TCID$_{50}$/mL) to $\frac{1}{10}$ of the original concentration ($2.5 \times 10^8$ TCID$_{50}$/mL)

A mixture of five sulfonated amino acids (2.0 g) prepared according to the method of Example 11 and sodium 2-cyclohexylbutyrate (8.0 g) were dissolved in 50 mL of the IBDV solution prepared above. 1 mL of a 0.5 mg/mL solution of cholera toxin β-subunit (CTB) and 0.25 mL of a 0.1 mg/mL solution of cholera holotoxin (CT) was added, and the resultant solution (solution 1) was warmed to 40° C. and incubated for 10 minutes.

50 mL of 1.7 N citric acid/1% gum acacia/2% β-cyclodextrin solution (solution 2) was warmed to 40° C.

Solutions 1 and 2 were mixed to provide a suspension of IBDV/CTB/CT containing microspheres.

Nineteen chickens were each dosed, by oral gavage, with 2 ml per bird of the microspheres suspension (prepared daily) on three consecutive days. Each daily dose contained $2.5 \times 10^8$ TCID$_{50}$/mL of IBDV, 10 µg of CTB, and 0.5 µg of CT.

After four weeks, each bird immunized as above and twenty-four unimmunized birds were challenged via intraocular administration of live IBDV. Four days after challenge the immunized birds, the unimmunized birds, and birds that were unchallenged and unimmunized were sacrificed, and their bursae were removed. Examination for gross bursal lesions and comparison among the three groups of birds revealed that all of the birds that were administered the microsphere suspension (the immunized/challenged birds, 19 of 19) were uninfected by IBDV upon challenge, while only 25% of the unimmunized/challenged birds (6 of 24) were uninfected after challenge.

All patents, applications, publications, and test methods cited herein are hereby incorporated by reference.

Many variations of the present invention will suggest themselves to those skilled in the art in light of the above detailed disclosure. All such modifications are within the full intended scope of the appended claims.

What is claimed is:

1. A composition comprising:
   (a) an antigen;
   (b) an adjuvant;
   (c) at least one carrier comprising a member selected from the groups consisting of:
      (i) an acylated amino acid or a salt thereof;
      (ii) a poly amino acid comprising at least one acylated amino acid or a salt thereof;
      (iii) a sulfonated amino acid or a salt thereof;
      (iv) a poly amino acid comprising at least one sulfonated amino acid or a salt thereof; or
      (v) any combination thereof.

2. A composition as defined in claim 1, comprising a mixture.

3. A composition as defined in claim 1, comprising a microsphere.

4. A composition as defined in claim 1, wherein said antigen comprises a peptide.

5. A composition as defined in claim 1, wherein said adjuvant comprises a mucosal adjuvant.

6. A composition as defined in claim 1, wherein said carrier comprises an acylated amino acid or a salt thereof.

7. A composition as defined in claim 1, wherein said carrier comprises a poly amino acid comprising at least one acylated amino acid or a salt thereof.

8. A composition as defined in claim 1, wherein said carrier comprises a sulfonated amino acid or a salt thereof.

9. A composition as defined in claim 1, wherein said carrier comprises a poly amino acid comprising at least one sulfonated amino acid or a salt thereof.

10. A composition as defined in claim 1, wherein said carrier is selected from the group consisting of, N-cyclohexanoyl arginine; a mixture of N-cyclohexanoyltyrosine and N-cyclohexanoylleucine; a mixture of N-phenylsulfonylvaline, N-phenylsulfonylleucine, N-phenylsulfonylphenylalanine, N-phenylsulfonyllysine, and N-phenylsulfonylarginine; and a mixture of N-benzoylvaline, N-benzoylleucine, N-benzoylphenyl-alanine, N-benzoyllysine, and N-benzoylarginine.

11. A dosage unit form comprising
   (A) a composition according to claim 1; and
   (B)
      (a) an excipient,
      (b) a diluent,
      (c) a disintegrant,
      (d) a lubricant,
      (e) a plasticizer,
      (f) a colorant,
      (g) a dosing vehicle, or
      (h) any combination thereof.

12. A dosage unit form according to claim 11 comprising a tablet, a capsule, or a liquid.

13. A method for administering an antigen to an animal, said method comprising orally administering a composition as defined in claim 1.

14. A method for preparing a composition as defined in claim 1, said method comprising mixing an antigen, an adjuvant, and a carrier comprising a member selected from the group consisting of:
  (i) an acylated amino acid or a salt thereof;
  (ii) a poly amino acid comprising at least one acylated amino acid or a salt thereof;
  (iii) a sulfonated amino acid or a salt thereof;
  (iv) a poly amino acid comprising at least one sulfonated amino acid or a salt thereof; or
  (v) any combination thereof.

* * * * *